United States Patent [19]
DeHart

[11] Patent Number: 5,454,381
[45] Date of Patent: Oct. 3, 1995

[54] SURGICAL DRAPE AND METHOD OF MAKING A SURGICAL DRAPE

[75] Inventor: Henry DeHart, Columbus, Mo.

[73] Assignee: Boundary Healthcare Products Corporation, Columbus, Miss.

[21] Appl. No.: 183,978

[22] Filed: Jan. 21, 1994

Related U.S. Application Data

[62] Division of Ser. No. 814,474, Dec. 30, 1991, Pat. No. 5,341,821.

[51] Int. Cl.$^6$ .................................................. A61B 19/00
[52] U.S. Cl. ........................................ 128/849; 128/851
[58] Field of Search ...................................... 128/849–856

[56] References Cited

U.S. PATENT DOCUMENTS

| | | | |
|---|---|---|---|
| 3,503,391 | 3/1970 | Melges | 128/853 |
| 3,750,664 | 8/1973 | Collins | 128/853 |
| 3,856,005 | 12/1974 | Sislian | 128/853 |
| 4,570,628 | 2/1986 | Neal | 128/853 |
| 4,873,997 | 10/1989 | Marshall | 128/853 |
| 4,905,710 | 3/1990 | Jones | 128/853 |
| 5,074,316 | 12/1991 | Dowdy | 128/853 |
| 5,097,847 | 3/1992 | Mikhail | 128/853 |
| 5,143,091 | 9/1992 | Patnode | 128/853 |

Primary Examiner—Michael A. Brown
Attorney, Agent, or Firm—Oblon, Spivak, McClelland, Maier, & Neustadt

[57] ABSTRACT

A drape for performing a surgical procedure on a patient's body includes a sheet portion for placement on a surgical table, the sheet portion having a first and second side edge, and a transparent side portion connected to at least one of the first and second side edges of the sheet portion for allowing viewing of an area beneath the table by a surgeon or by surgical staff. The sheet portion is of a nonwoven material and the transparent side portion may be connected to each of the first and second side edges of the sheet portion by bonded seams. The sheet portion may include a reinforced portion and a fenestration located in the reinforced portion, as well as a fluid collecting pocket located along at least one side of the fenestration or reinforced portion. The sheet portion may also be T-shaped, depending upon the shape of the surgical table. A corresponding method of forming the drape is also disclosed.

10 Claims, 6 Drawing Sheets

SURGICAL DRAPE AND METHOD OF MAKING A SURGICAL DRAPE

This is a division of application Ser. No. 07/814,474, filed on Dec. 30, 1991, now U.S. Pat. No. 5,341,821.

BACKGROUND OF THE INVENTION

1. Field of the Invention

The present invention is directed to a surgical drape and method of making a surgical drape suitable for surgery, the center portion of which is formed of a nonwoven material and which has transparent side or lower portions connected to opposite sides of the nonwoven material for the purpose of allowing viewing of instruments or other apparatuses and control mechanisms beneath a table which may be utilized, for example, in surgery.

2. Description of the Prior Art

Prior art surgical drapes are known and are exemplified by U.S. Pat. No. 4,476,860 which discloses a surgical drape which includes a main sheet of flexible material having an inner surface for facing toward a patient after placement of the drape, and an outer surface facing away from the patient after displacement of the drape. The drape has a pair of pockets on the outer surface of the main sheet and includes an outer edge defining an opening of the pockets which face towards each other. This drape has the drawback, however, of not allowing for viewing of instruments or other apparatuses and control mechanisms which would be normally located beneath the surgical table. This can possibly lead to difficulties in terms of operation of control mechanisms during surgery or locating apparatuses which are of assistance to the surgeon or the surgeon's support staff during surgery.

SUMMARY OF THE INVENTION

One object of the present invention is to provide a drape for performing surgical procedures on a patient's body which includes a sheet portion for placement on a patient lying on a surgical table, the sheet portion having a first and second side edge, and a transparent side portion connected to at least one of opposed first and second side edges of the sheet portion for allowing viewing of an area beneath the table to assist the surgeon and/or the surgeon's support staff during surgery.

A further object of the invention is to provide the sheet portion with a reinforced portion and an elongated or longitudinally extending fenestration formed in the reinforced portion. The fenestration allows a specific area of the patient to be exposed for a variety of surgical procedures.

An additional object of the invention is to provide a surgical drape wherein the reinforced portion has fluid collecting pockets, pouches or troughs formed at least along one side of the reinforced portion or the fenestration formed in the reinforced portion to catch fluid runoff from the surgical site would otherwise obscure the visibility characteristics of the transparent side portions if the fluid were allowed to drain off from the table.

A yet further object of the invention is to provide a sheet portion which is T-shaped so as to fit over an operating table which has armboards and to provide a sheet which may have a slit portion at one end thereof which allows for an extremity of a patient to be exposed therethrough for a surgical procedure.

A further object of the invention is to provide a drape which has a nonwoven material portion which includes a reinforced portion for covering a portion of a patient to be operated on or to provide a nonwoven material portion of the sheet which includes a reinforced portion wherein an elongated or longitudinally extending slit is formed in the reinforced portion.

Lastly, a yet further object of the invention is to provide a sheet wherein a nonwoven material portion thereof includes a reinforced portion, a slit formed in the reinforced portion and fluid collecting means located on the reinforced portion and positioned along at least one side of the slit.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
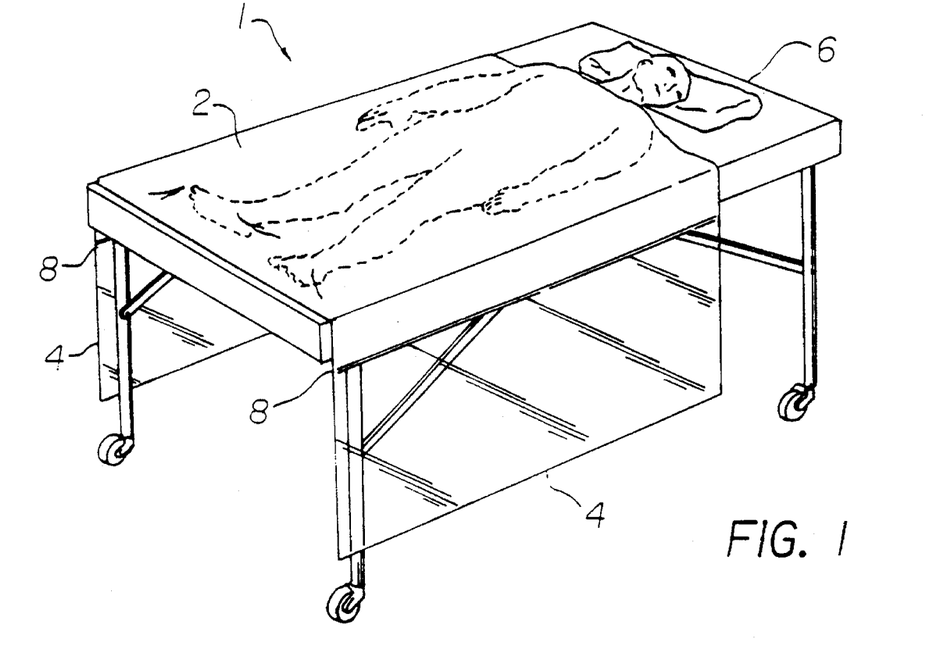
FIG. 1 illustrates a first embodiment of the invention showing a surgical drape with clear or transparent sides.

FIG. 1 illustrates a surgical drape 1 suitable for surgery, the main sheet or center portion 2 of which is made of nonwoven material (i.e., hydroentangled wood pulp/polyester, wet laid wood pulp/polyester, wood pulp, polyester, spunbonded polypropylene or ethylene, spunbonded/meltblown/spunbonded polypropylene, poly amide or other similar materials or combination thereof that are not woven or knitted and do not require converting fibers to yarn) which has side portions 4, 4 attached to the nonwoven center portion 2 on one or both sides thereof. The side portions are those portions of the drape that extend from approximately the upper edge portion of the operating table downwardly to the floor. The side portions are also those portions of the drape along opposite lateral sides of the length dimension of the drape, as compared with the shorter opposed end portions as can be appreciated from a review of FIG. 1. One or both of the side portions 4, 4 are formed of a clear or transparent plastic material (i.e., polyethylene, polypropylene, ethylene vinyl acetate or other material which is of polymer construction).

It is also to be noted that nonwoven fabrics are broadly defined as including sheet or web structures made by bonding or entangling fibers or filaments (and by perforating films) by mechanical, thermal or chemical means as defined in *THE NONWOVENS HANDBOOK* of the Association of the Nonwoven Fabrics Industry, pages 9–11, and authored by Dr. Bernard Lichstein copyright 1988.

The transparent side portions 4, 4 are for the purpose of viewing instruments or other apparatuses (i.e., fluid collection suction canisters, urine collection bags, oxygen/nitrous oxide connections) and controls (e.g., foot pedals for changing the table). This allows the surgical staff to observe any area under the table. The clear plastic material could also have physical properties which would be different than those of the nonwoven central portion (i.e., with improved flammability properties or non-flaming characteristics which are not possible in nonwoven material without the use of treatments which can be injurious to areas contacting the skin of a patient).

The side portions 4, 4 are fixedly attached along bonded seams 8, 8 by use of adhesives, glue, heat, tape, ultrasonics or by other suitable means. A surgical drape of the above-noted description allows for covering part or all of the patient 12. This drape would be used for surgery where the operative site need not be exposed through the drape.

Figure 2:
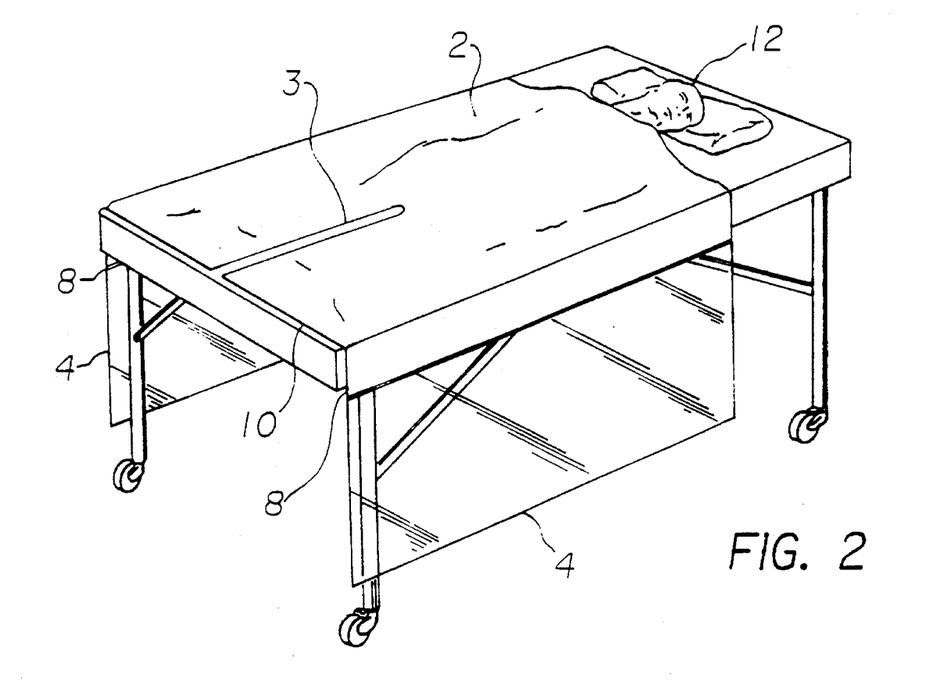
FIG. 2 illustrates a surgical drape with clear or transparent sides wherein a slit or U-shaped fenestration is formed at one end of the drape.

FIG. 2 illustrates a second embodiment of the present invention wherein the surgical drape 1 has a center portion 2 which is made of a nonwoven material as explained in connection with FIG. 1 and which also includes an elongated or longitudinally extending slit or split 3 which has been cut from one end 10 of the drape. This allows for an extremity of the patient to be exposed through the slit for a surgical procedure. This may also be used to expose some portion of the main body area of the patient.

Figure 3:
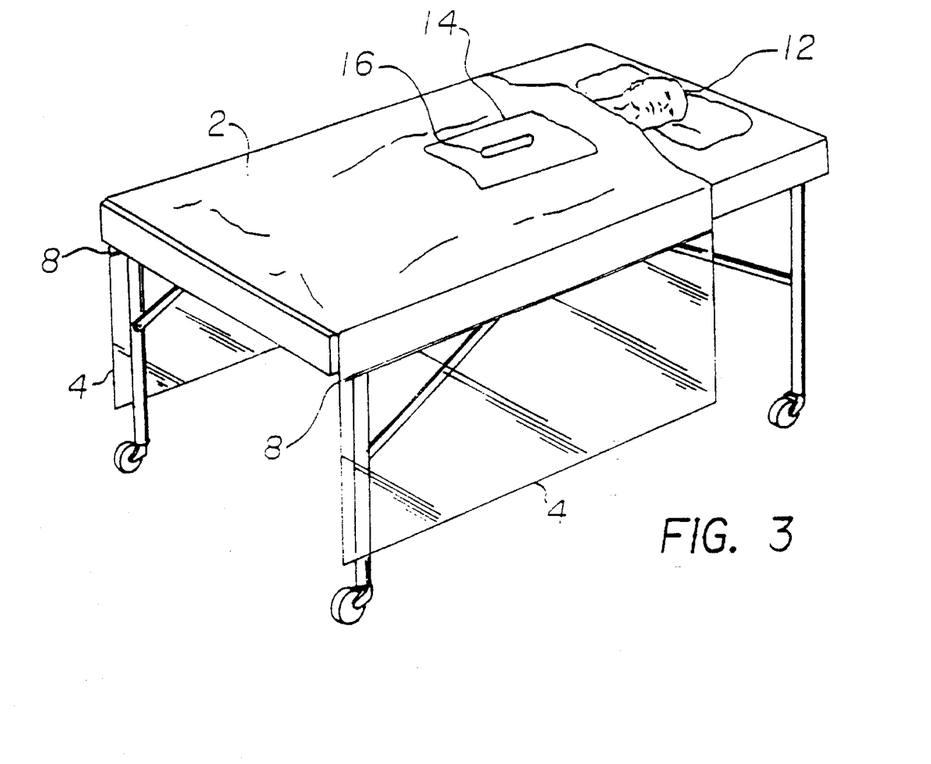
FIG. 3 illustrates an additional embodiment of the invention which utilizes a surgical drape having clear or transparent sides in addition to a reinforced surgical fenestration.

A further embodiment of the surgical drape 1 suitable for surgery is shown in FIG. 3 which illustrates a reinforced area 14 through which an elongated or longitudinally extending fenestration 16 has been cut. The fenestration 16 would allow a specific area of the patient to be exposed for a surgical procedure.

Figure 4:
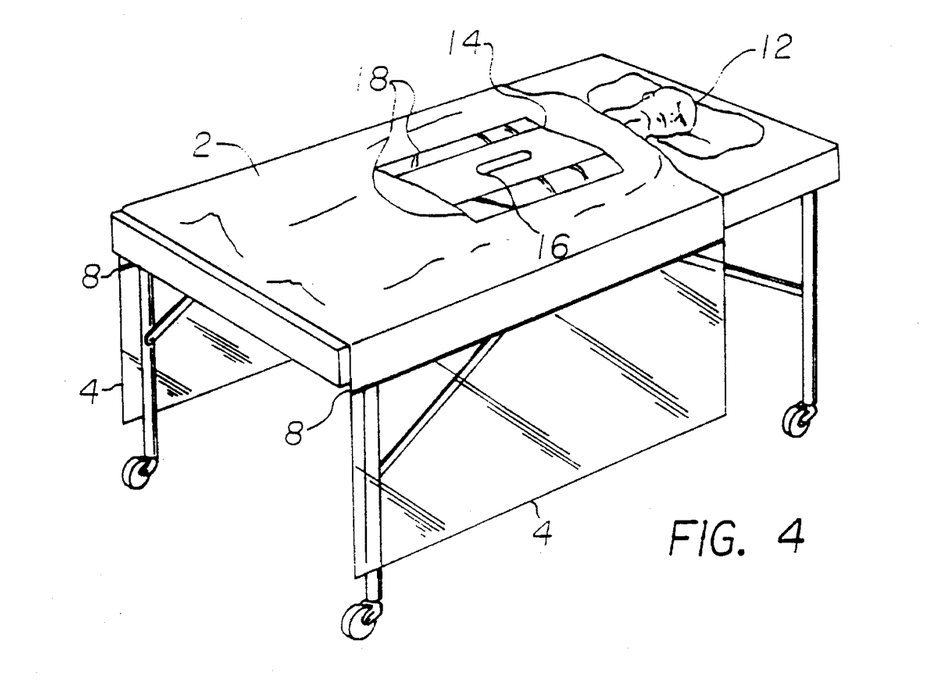
FIG. 4 shows a surgical drape having transparent sides in combination with a reinforced surgical fenestration that incorporates pockets for the collection of fluid runoff.

In FIG. 4, a surgical drape as described in FIG. 3 is illustrated but which also includes pockets, pouches or troughs 18 made from any suitable material which is placed is proximity to and is open towards the fenestration 16 to catch fluid runoff from the surgical site which would otherwise obscure the visibility characteristics of the clear side portions 4, 4 if allowed to drain off the table. The pockets 18 are located on opposite sides of the reinforcement 14, may be made from any suitable material and are constructed to catch fluid runoff for removal by appropriate means such as a suction member or drainage line. The pockets 18 can be located on one side, both sides, or can be located so as to be continuous around the fenestration 16.

Figure 5:
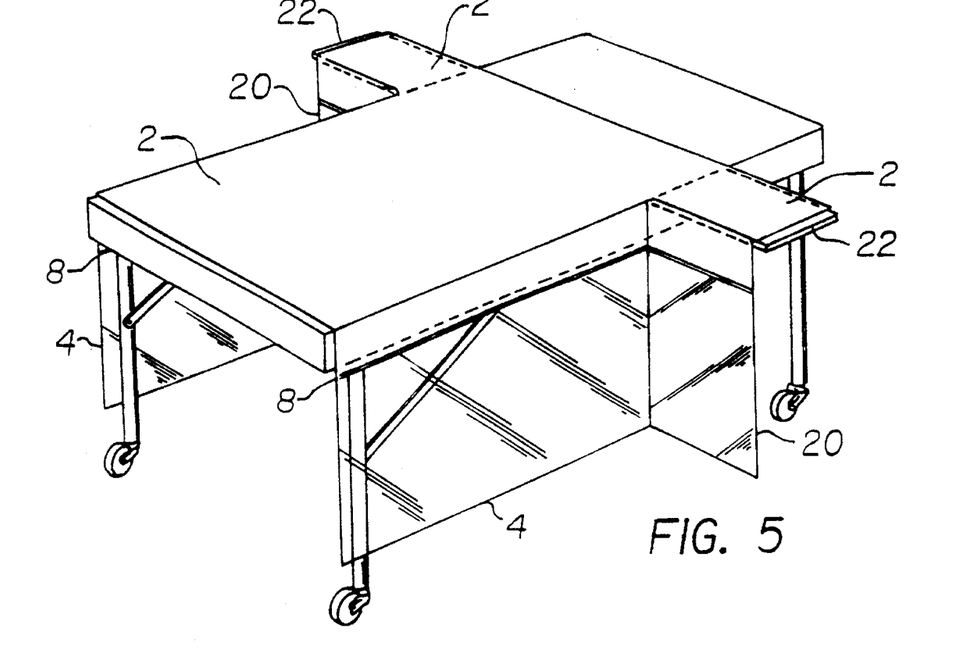
FIG. 5 illustrates a drape having a T-shape for being placed on a surgical table having armboards, the drape including clear or transparent sides and arm portions to cover the armboards.

With regard to the embodiment in FIG. 5, the surgical drape is similar to that shown in FIG. 1 but includes transparent extensions 20, 20 attached to nonwoven portions 2, 2 which cover armboards 22, 22 of the operating table. The armboards are used when it is necessary to extend one or both arms of the patient. The result is that both the surgical drape and the table are of a T-shape.

Figure 6:
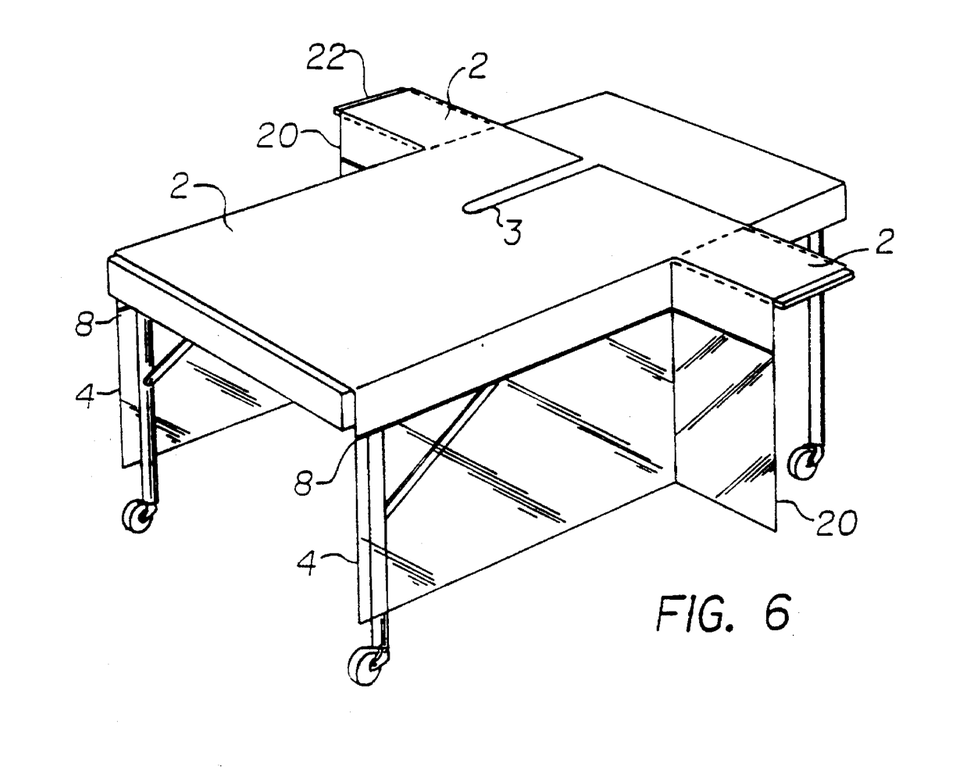
FIG. 6 illustrates a drape similar to that of FIG. 5 but which includes a split or U-shaped fenestration at one end thereof.

In the embodiment shown in FIG. 6, a surgical drape 1 is shown which corresponds to that illustrated in FIG. 5 but which also includes a slit 3 in addition to the extensions 20, 20 which cover the armboards 22, 22 of the operating table so as to be T-shaped.

Figure 7:
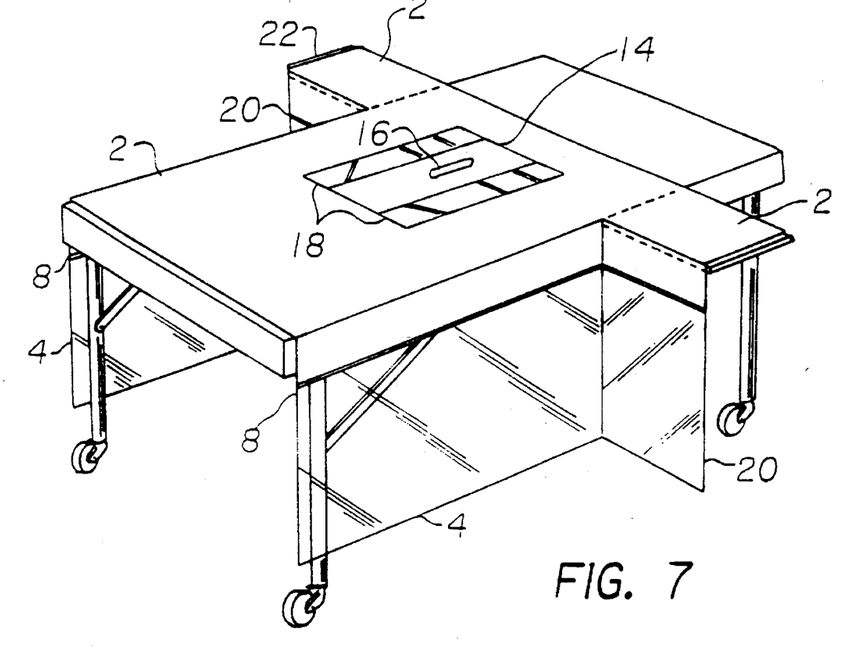
FIG. 7 shows a surgical drape similar to that of FIG. 5 but which includes a reinforced surgical fenestration that utilizes pockets for collection of fluid runoff from a surgical site.

A surgical drape is also shown in FIG. 7 which includes structure similar to that shown in FIG. 4 in addition to having armboards 22, 22 and drape extensions 20, 20. That portion of the drape which covers the armboards 22, 22 is preferably of nonwoven material 2.

Figure 8:
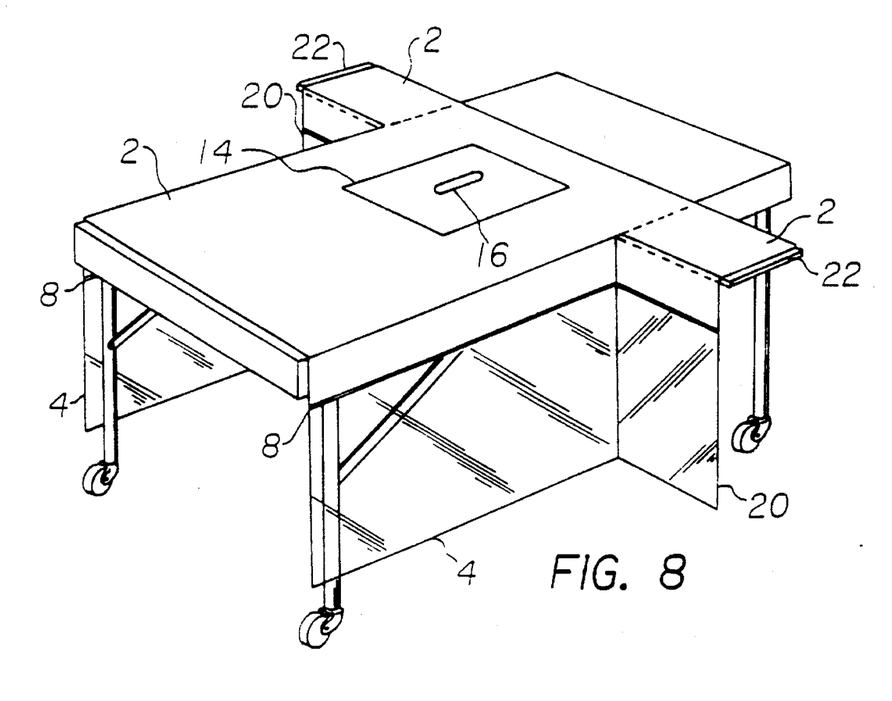
FIG. 8 shows a surgical drape similar to that of FIG. 5 but which includes a reinforced surgical fenestration.

With regard to the embodiment shown in FIG. 8, this illustrates a surgical drape similar to that shown in FIG. 3 but with the addition of armboards 22, 22 and extensions 20, 20 such as described in FIG. 6.

Figure 9:
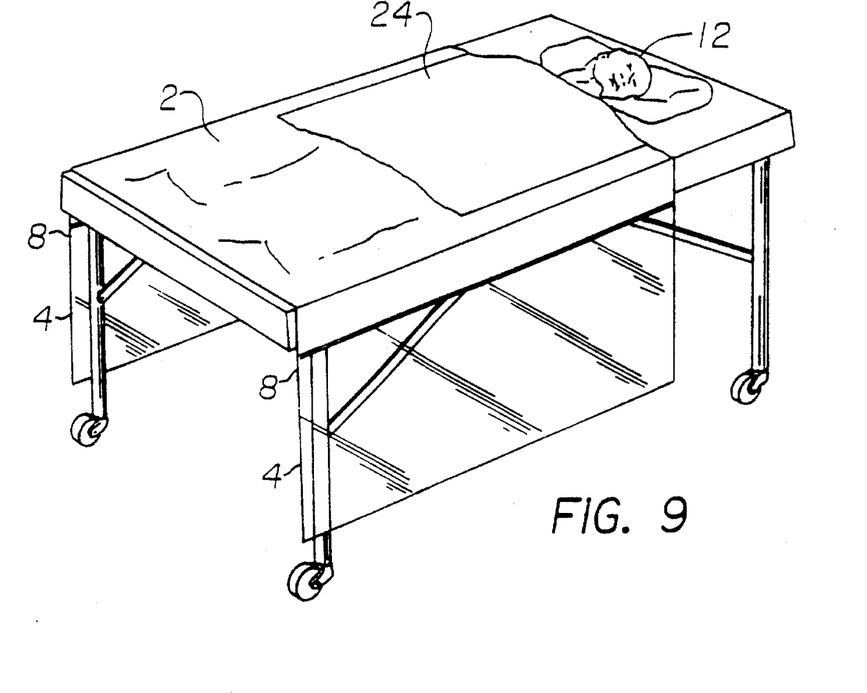
FIG. 9 illustrates a surgical drape with a reinforced area for covering part or all of the patient.
Figure 10:
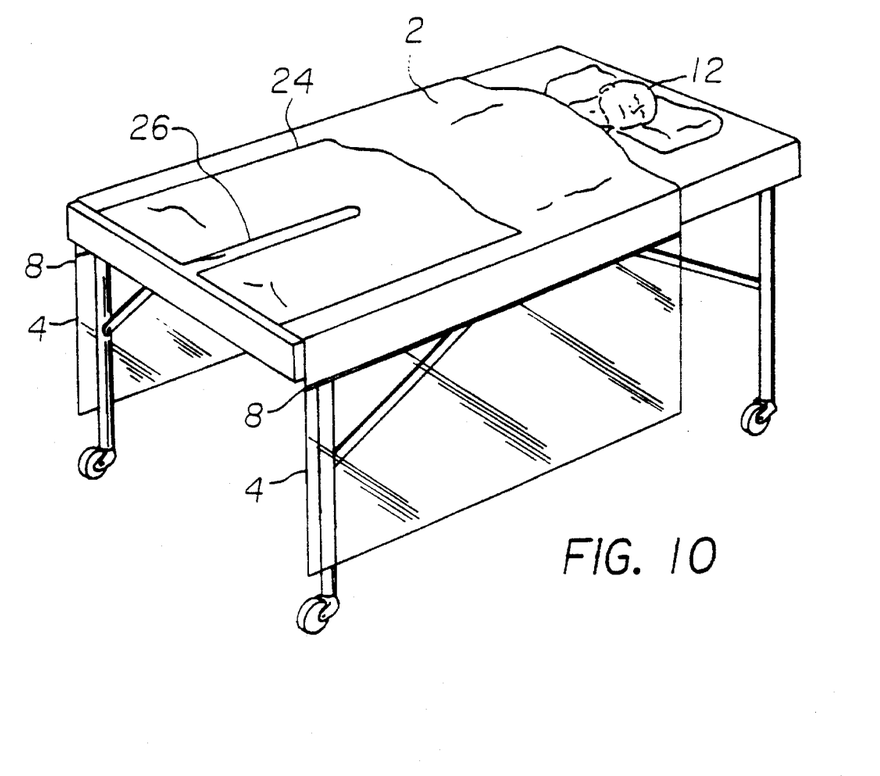
FIG. 10 illustrates a surgical drape wherein a slit is provided at one end of a reinforced area so as to allow for an extremity of the patient to be exposed through the slit for a surgical procedure.

A further embodiment of the surgical drape 1 is shown in FIG. 9 which has a reinforced area 24 for covering part or all of the patient 12. This drape would, for example, be used for surgery where the operational site need not be exposed or would be used when the surgeon cuts an opening through the reinforced portion to expose a surgical site of the patient. As shown, the sheet completely covers the table and the boarded seams are at a location opposite the lower edge portion of the table. In FIG. 10, the surgical drape includes a slit or split 26 which has been cut from one end 11 of the reinforced area 24. This would allow for an extremity of the patient to be exposed through the slit 26 for a surgical procedure. This may also be used to expose a portion of the main body area of the patient 12.

Figure 11:
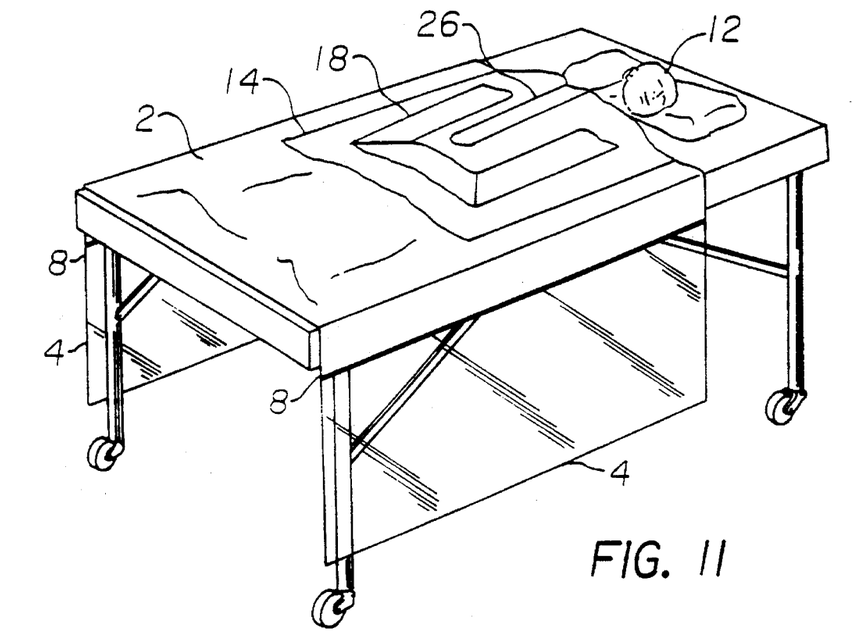
FIG. 11 shows a surgical drape having pockets, pouches or troughs located on a reinforced area and which at least partially surround a slit formed in the reinforced area.

A yet further embodiment of the present invention is illustrated in FIG. 11 which shows a surgical drape which includes one or more pockets, pouches or troughs 18 made from any suitable material for collecting fluid and which is located in proximity to a slit 26 for catching fluid runoff from the surgical site which would otherwise obscure the visibility characteristics of the clear lower portions if allowed to drain off the table. The pockets 18 are constructed to catch fluid runoff for removal by a mechanism such as the suction member or a drainage line previously mentioned. The pockets 18 can be located on one side, both sides or extend continuously around the split 26.

Figure 12:
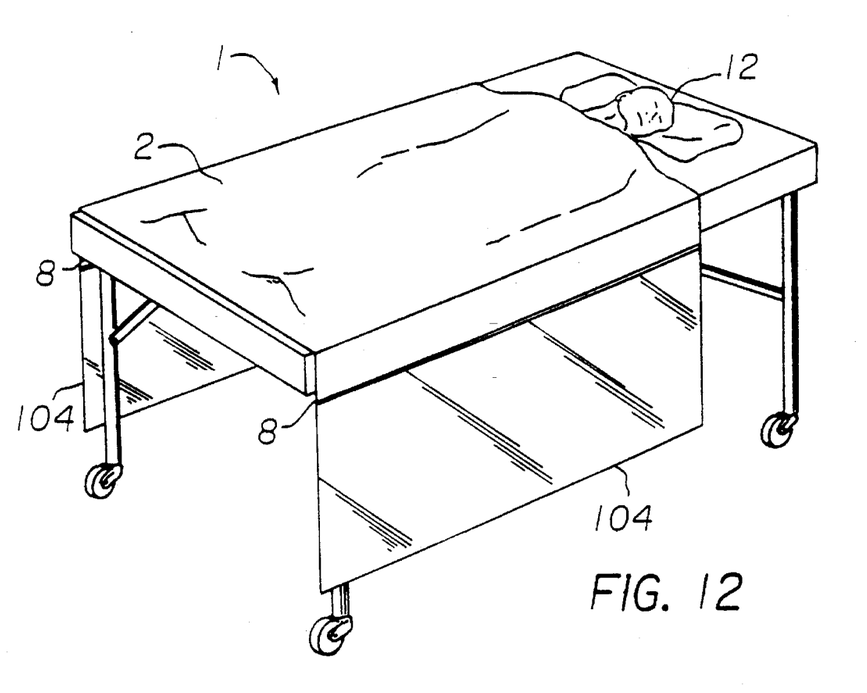
FIG. 12 shows a surgical drape with non-transparent sides.

Lastly, FIG. 12 shows an embodiment like that of FIG. 1, but wherein the sides 104 of similar composition to that of sides 4, but which are not transparent. Sides 104 can, of course, be substituted for sides 4 in any of FIGS. 1–11.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A drape for performing a surgical procedure on a patent's body, which comprises:

a nonwoven and nontransparent sheet portion for placement on a surgical table, said sheet portion having a side edge wherein said side edge is substantially planar, hangs over a side portion of the table and extends to a location in proximity with a lower side edge portion of the table; and a transparent side portion connected to said side edge of said sheet portion wherein said transparent side portion is substantially planar and overhangs a side of the table for allowing viewing of an area beneath the table and wherein said sheet portion has a reinforced portion.

2. A drape as claimed in claim 1, wherein said transparent side portion is connected to each of said first and second side edges of said sheet portion.

3. A drape as claimed in claim 1, which comprises a connection for fixedly connecting said transparent side portion by bonded seams to said at least one of said first and second side edges of said sheet portion.

4. The drape as claimed in claim 1, wherein said side edge is located opposite the lower edge portion of the table such that the sheet portion completely covers the table.

5. A method of making a surgical drape for a surgical table, which comprises:

making a portion of the drape with a nonwoven and nontransparent material and dimensioning said drape such that a side edge thereof is substantially planar, extends to a location overhanging a side portion of the table and extends to a position in proximity with a lower edge portion of the table; and connecting at least one substantially planar side portion of said nonwoven material with a substantially planar transparent side portion such that said transparent side portion overhangs the side of the table and an area beneath said table is made visible.

6. A method as claimed in claim 5, which comprises making a portion of the nonwoven material of a reinforced material.

7. The method as claimed in claim 5, wherein said dimensioning of said drape comprises dimensioning the drape such that the nonwoven portion completely covers the table.

8. A drape for performing a surgical procedure on a patent's body, which comprises:

a nonwoven and nontransparent sheet portion for placement on a surgical table, said sheet portion having a side edge wherein said side edge is substantially planar and extends to a location overhanging a side portion of the table and in proximity with a lower edge portion of the table; and a substantially planar, transparent side portion connected to at a side edge of said sheet portion such that said transparent side portion overhangs a side of the table for allowing viewing of an area beneath the table wherein said sheet portion has a reinforced portion.

9. A drape as claimed in claim 8, wherein said nonwoven material includes a reinforced area.

10. The drape as claimed in claim 8, wherein said side edge is located opposite the lower edge portion of the table such that the sheet portion completely covers the table.

* * * * *

UNITED STATES PATENT AND TRADEMARK OFFICE
CERTIFICATE OF CORRECTION

PATENT NO. : 5,454,381
DATED : October 3, 1995
INVENTOR(S) : Henry DEHART

It is certified that error appears in the above-indentified patent and that said Letters Patent is hereby corrected as shown below:

On the title page, Item [75], the inventor's address should read:

--Columbus, MS--

Signed and Sealed this

Twenty-third Day of January, 1996

Attest:

BRUCE LEHMAN

Attesting Officer

Commissioner of Patents and Trademarks